(12) United States Patent
Ardizzone (10) Patent No.: US 6,971,984 B2
(45) Date of Patent: Dec. 6, 2005

(54) MAGNETO-CYMATIC THERAPEUTIC FACE MASK

(75) Inventor: Vincent Ardizzone, 9 Stuarts Ct., Port Jefferson, NY (US) 11777

(73) Assignee: Vincent Ardizzone, Port Jefferson, NY (US)

( * ) Notice: Subject to any disclaimer, the term of this patent is extended or adjusted under 35 U.S.C. 154(b) by 0 days.

(21) Appl. No.: 10/893,120

(22) Filed: Jul. 15, 2004

(65) Prior Publication Data

US 2005/0038313 A1 Feb. 17, 2005

Related U.S. Application Data

(63) Continuation-in-part of application No. PCT/US03/04546, filed on Feb. 12, 2003.

(51) Int. Cl.[7] ................................................. A61N 2/00
(52) U.S. Cl. ........................................................ 600/9
(58) Field of Search .................. 600/9–15; 601/46–83, 601/89–93

(56) References Cited

U.S. PATENT DOCUMENTS 5,642,739 A * 7/1997 Fareed ........................ 128/881
5,738,624 A * 4/1998 Zablotsky et al. .............. 600/9
6,182,313 B1 2/2001 Eschenbach .................... 5/640

FOREIGN PATENT DOCUMENTS

| DE | 25 20 108 | 5/1975 |
| DE | 34 27373 A1 | 7/1984 |
| DE | 37 19331 A1 | 6/1987 |
| DE | 196 13 425 A1 | 4/1996 |

OTHER PUBLICATIONS

Raphael, Cymatics Today with Elizabeth Colorio, Spirit of Ma'at: "Music of the Spheres"; vol. 3 Oct. 2002.*

* cited by examiner

*Primary Examiner*—John P. Lacyk
(74) *Attorney, Agent, or Firm*—Orrick Herrington & Sutcliffe LLP (57) ABSTRACT

A face mask that delivers magneto-cymatic therapy to a person's face to treat wrinkles and to tone facial muscles. The device consists of a mask worn over the face. Housed within the mask is an array of small transducers delivering cymatic vibrations. At the center of each transducer is a strong permanent magnet which delivers the magnetic therapy. Both the cymatic vibrations and the magnetic field are delivered concurrently. In addition, the magnetic field serves as a conduit for the cymatic vibrations providing a magnetic inductive coupling with the cells in the facial tissue to assist in restoring the cells to their proper resonant frequency.

12 Claims, 7 Drawing Sheets

MAGNETO-CYMATIC THERAPEUTIC FACE MASK

CROSS REFERENCE TO RELATED APPLICATIONS

This application is a continuation-in-part of P.C.T./U.S. patent application Ser. No. 03/04546 filed Feb. 12, 2003 which application is incorporated herein by this reference hereto.

BACKGROUND OF THE INVENTION

1. Field

The present invention relates to a therapeutic device that is intended to simultaneously apply magnetic therapy with cymatic therapy to an anatomical area to be treated.

2. State of the Art

The therapeutic use of devices delivering cymatic vibrations to treat certain ailments and debilitating conditions is known. Cymatic therapy is based on the principal that every cell in the body is enveloped by an electromagnetic field that resonates at its own particular sound frequency. Around 850 cymatic frequencies have been discovered over the years. When the body is well these frequencies are steady and constant, but any dysfunction or disease upsets the harmony of the body and the effected areas then generate off-resonance frequencies. Cymatic therapy aims to generate a frequency identical to that of healthy cells. The aim is to support what the cells are trying to do naturally, thereby aiding the healing process and restoring the body to good health and harmony.

The therapeutic use of magnetic fields in treating various conditions is also well known. The beneficial effects of applying a magnetic field to an area of human and animal anatomy such as the back, legs, arms and the like, are widely known and well documented. Magnetic fields are commonly used for therapeutic purposes such as reduction of inflammation in tissues and pain relief. Although it is not entirely clear how magnetic therapy works, it has been found to increase blood flow and therefore oxygen carrying capacity, to change the migration of calcium ions to or from the bone, to alter the pH balance of various body fluids, to alter hormone production from endocrine glands and to alter the enzymatic activity and other biochemical processes of the human body.

Many therapeutic devices are available which apply magnetic therapy to an anatomical area such as the muscles of the lower back to enhance circulation and relax such muscle. Indeed, many therapeutic devices are known which combine magnetic therapy with vibratory massage, heat, infrared, or sound, or a combination of same. Ardizzone in U.S. Pat. No. 6,383,129 discloses a magnetotherapeutic device which combines magnetotherapy in conjunction with infrared therapy. Souder in U.S. Pat. No. 6,231,497 discloses a magnetic therapy device which combines a dynamic magnetic field in conjunction with vibratory massage. Eschenbach in U.S. Pat. No. 6,182,313 discloses a magnetic therapy head cradle apparatus which combines a sound system in the head cradle with the magnetic field. Franco-Vila in U.S. Pat. No. 4,177,796 discloses a magnetic thermal vibrational device which simultaneously applies electromagnetic alternating directional energy, thermal, and vibrational energy to various areas of the body to reduce or eliminate the pains and symptoms of arthritis.

Although these various prior art devices apply magnetic therapy in combinations with vibration, heat and sound, none of the prior art devices apply a magnetic field in conjunction with cymatic vibration. Although both magnetic therapy and cymatic therapy have each been utilized to treat an effected area, the combination of the two therapies delivered by the single therapeutic device of the invention provides additional beneficial effects to the user as the treated area receives both cymatic vibrational therapy to re-establish cellular resonance to treat a specific condition and magnetic stimulation to enhance blood flow. Cymatic frequencies are delivered both by mechanical vibration and by the vibrating magnetic field by inductively linking with the cell's own electromagnetic field. This novel combination of cymatic vibrations with a magnetic field provides a superior mode of therapy that can conveniently be applied over most areas of the entire body.

OBJECTS AND SUMMARY OF THE INVENTION

It is therefore, an object of the present invention to provide an improved device for therapeutic treatment of tissue by combining magnetic therapy using a strong magnet and cymatic therapy by providing a transducer which generates vibrations at a plurality of frequencies, simultaneously or alternatively, in accordance with the requirements of the operator.

It is yet another object of the invention to combine magnetic therapy and cymatic therapy in an integral and consolidated portable device that is convenient to use and does not require a direct mechanical linkage to the body.

The present invention relates to a therapeutic device and process for the application of cymatic and magnetic therapy simultaneously through the use of a mask-like apparatus or an undulating wand applied directly to or close to the body.

Broadly, one aspect of the invention relates to an apparatus for therapeutic treatment of a person's body comprising a wand-like applicator with a flexible application surface, at least one rare earth permanent magnet coupled to a transducer that converts cymatic sound frequencies to mechanical vibrations, and a Central Processing Unit ("CPU") that produces electrical signals at selected cymatic sound frequencies that is electrically connected to the transducer.

The invention also provides an apparatus for treating various injuries and/or disease conditions, comprising a wand-like device capable of generating cymatic vibrations simultaneously with a strong magnetic field and locatable in direct contact with or above the skin of an affected body part. Advantageously, the present invention provides a portable therapeutic device, having a handheld wand-like applicator that can be applied to any part of the body and provides vibration corresponding to an adjustable range of cymatic frequencies in combination with magnetic therapy.

A second embodiment of the present invention also provides an apparatus for treating facial wrinkles and to tone facial muscles, comprising a mask-like apparatus capable of generating cymatic vibrations simultaneously with a strong magnetic field and locatable in direct contact with or above the skin of the face.

BRIEF DESCRIPTION OF THE DRAWINGS

Further features, benefits, and advantages of the present invention will be apparent from a review of the following detailed description and accompanying drawings, in which like reference characters refer to like elements, and in which.

DETAILED DESCRIPTION OF THE INVENTION

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the embodiments which are described for purposes of illustration and not of limitation. However, it is to be understood that the same or equivalent functions and sequences may be accomplished by different embodiments that are also intended to be encompassed within the spirit and scope of the invention, and that particular values and measures may be varied without departing there from.

The Figures show different views of two embodiments of the magneto-cymatic therapeutic device of the present invention. The first embodiment of the present invention is applicable to a wide variety of disease conditions such as musculoskeletal injuries, rheumatoid joint conditions, lower back pain, and carpal tunnel syndrome. The second embodiment of the present invention is also applicable to a wide variety of facial conditions including musculoskeletal facial injuries, the treatment of wrinkles and the toning of facial muscles.

The present invention broadly provides for treating disease conditions by positioning the therapeutic apparatus of the invention directly in contact with the skin or directly above the skin over an affected body part. In a first preferred embodiment, with reference to FIGS. 1 and 2, an application surface (3) is mounted on a wand-like applicator (4) which fits into a wand housing (9) and is provided in different shapes to allow maximum contact between the application surface (3) and the contours of the body part to be treated (not shown). In alternate embodiments, different shapes and sizes of the wand-like applicator (4) are possible to better accommodate different parts of the body, e.g., a smaller wand and applicator head for treating the smaller muscles of the face. The wand housing (9) functions to provide a convenient mechanism to hold the applicator and for aesthetic purposes. The applicator-wand housing (9) and applicator-wand (4) are constructed of non-magnetic material. In the preferred embodiment a magnetic field is generated by at least one powerful permanent magnet (7) situated close to the surface of and centered on the application surface (3) of the applicator-wand (4). The magnetic field provided has a magnetic strength within the range of 300 to 3000 gauss, preferably 3000 gauss, as measured at the magnet surface by a Gaussmeter. The magnetic field is generated by a strong permanent magnet selected from such materials as neodynium (Nd), samarian cobalt, ferrite, or alnico. Neodynium is preferred as it provides the most powerful magnetic material. An electric coil may be used instead of a permanent magnet to produce an oscillating electromagnetic field; further providing the ability to produce a magnetic field of variable strength. However, the level of current required to produce a magnetic field of comparable strength to a high power permanent magnet is not as practical because the size of wire and number of turns required would adversely effect the operation of the transducer mechanism. In the preferred embodiment the magnetic field will concurrently oscillate at the prescribed cymatic frequencies.

Figure 1:
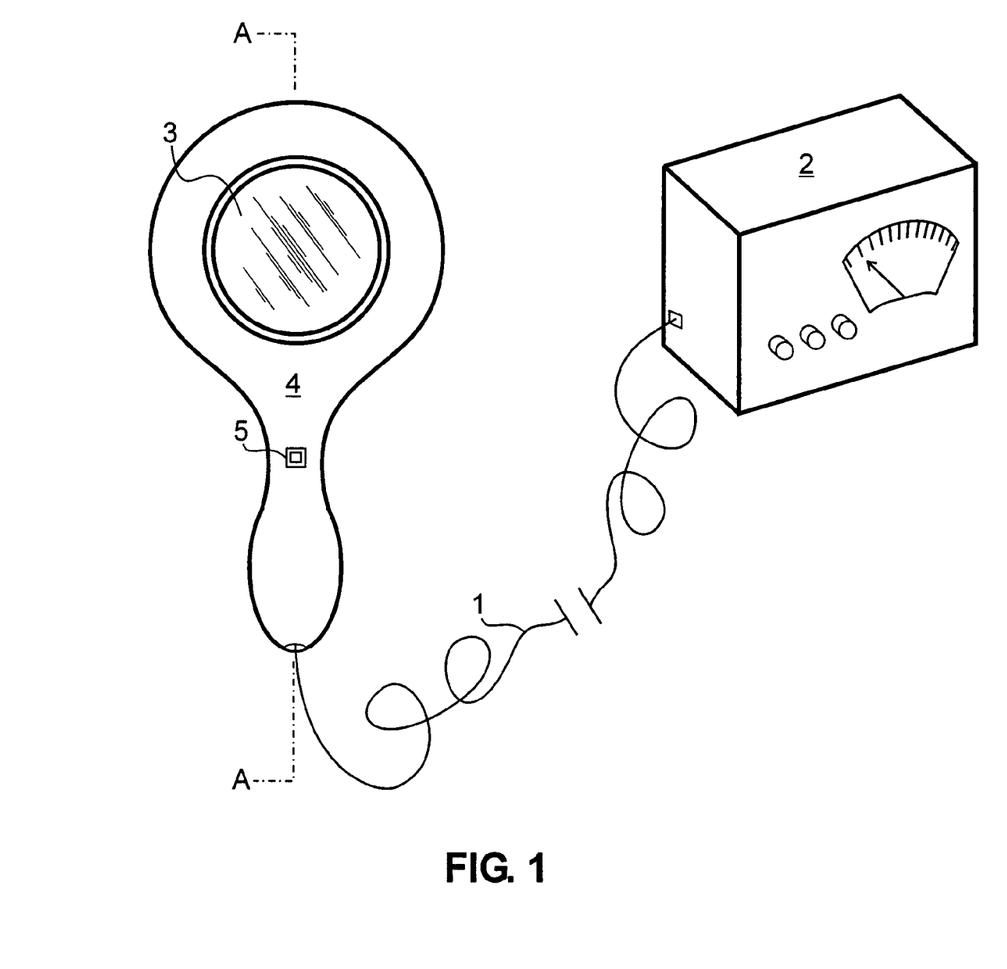
FIG. 1 is a perspective view of an apparatus according to a preferred embodiment of the present invention.
Figure 2:
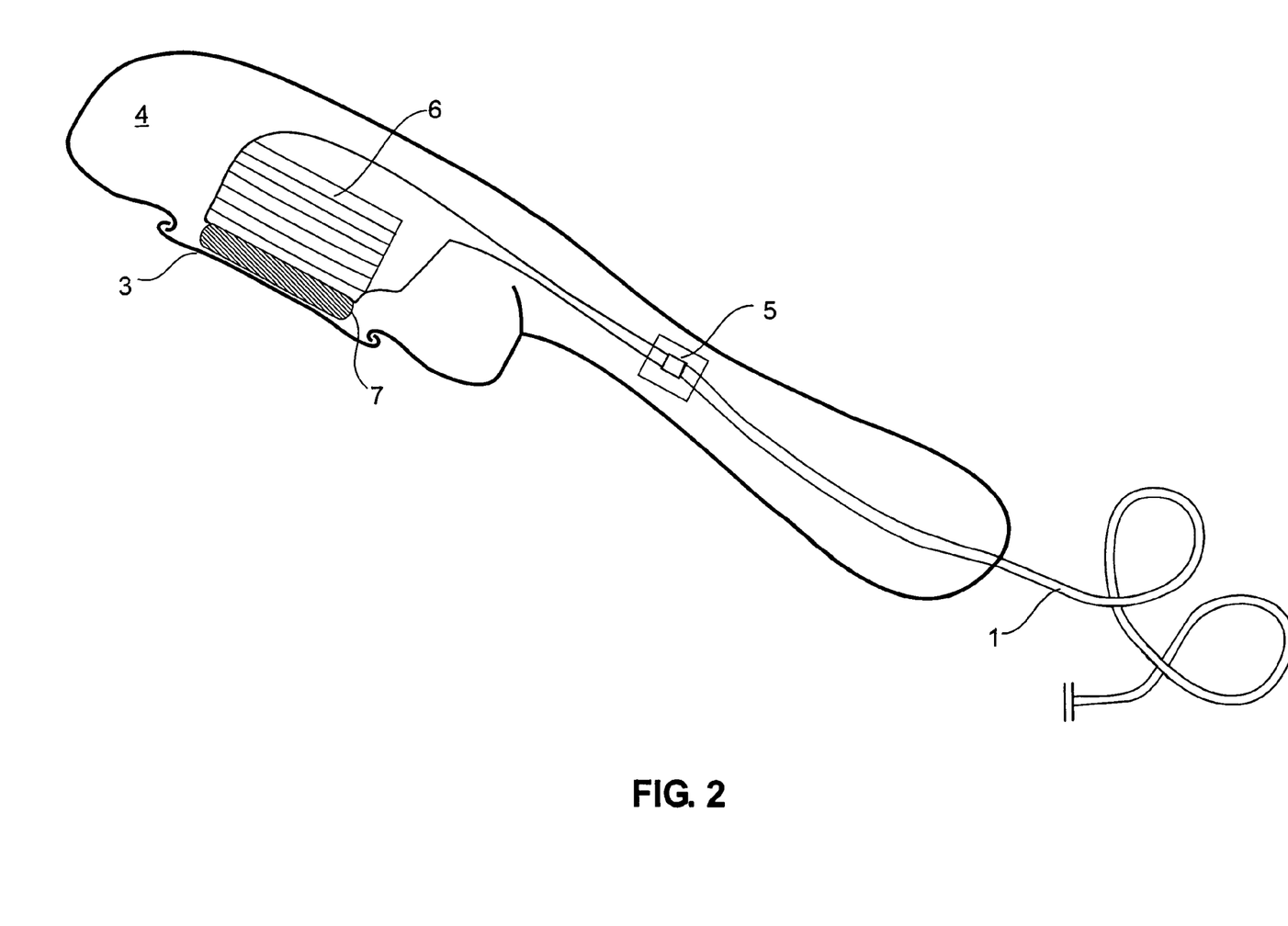
FIG. 2 is a section view taken along lines A—A of FIG. 1.
Figure 3:
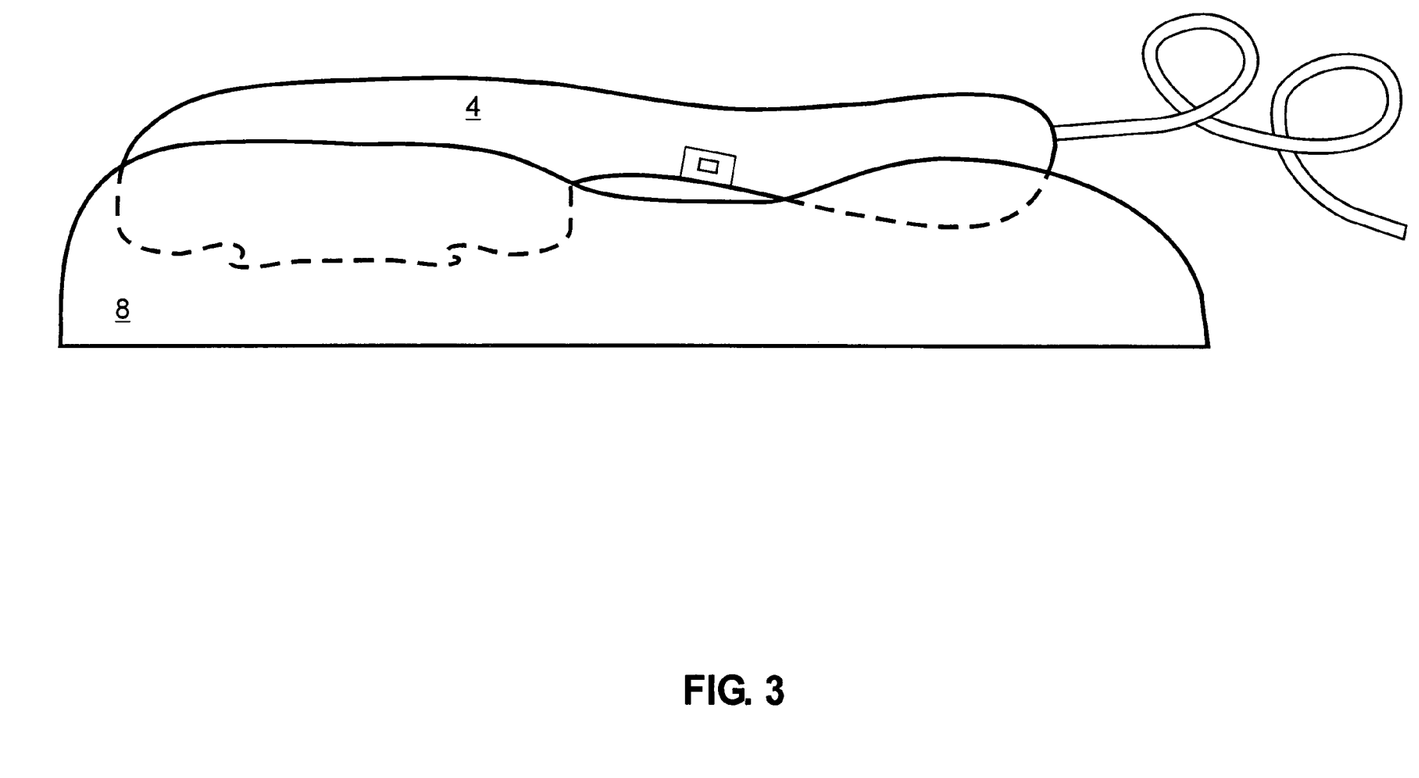
FIG. 3 is a side view of the wand-like applicator of FIG. 1, seated in a wand housing.
Figure 4:
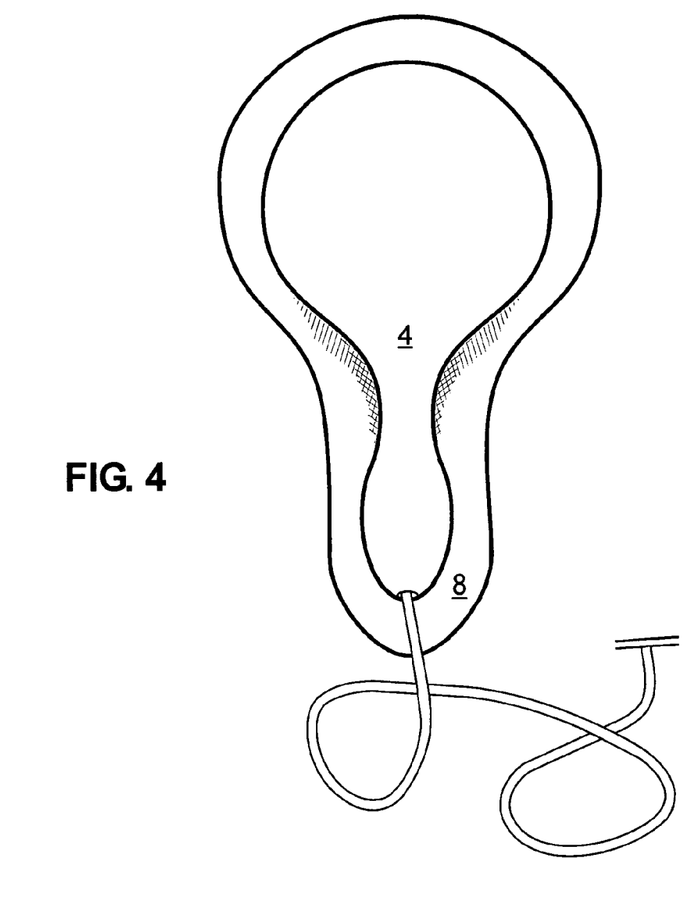
FIG. 4 is a top view of FIG. 3.

The cymatic frequencies are generated from electrical signals produced at audio frequencies by a Central Processing Unit (2) and transmitted to a transducer (6) contained within the applicator-wand (4). Transducer (6) converts the electrical signals to mechanical vibrations which cause the application surface (3) to oscillate according to selectable sound wave (cymatic) frequencies, and thereby provide cymatic treatment when the applicator-wand is applied directly in contact with specific areas of the body. The cymatic frequencies are preferably preset. Another mode of treatment involves applying the applicator-wand (4) above the body part to be treated but without directly contacting the skin. The magnetic filed emanating from the applicator-wand and vibrating at the frequencies generated by the transducer can penetrate the tissue and deliver cymatic therapy in conjunction with magnetic therapy by induction with the electromagnetic frequency of the tissue being treated without the need for the apparatus to contact the body. The strength of the magneto-cymatic therapy so delivered may be varied by varying the distance that the applicator-wand is held above the skin.

The simultaneous application of the strong magnetic field with the cymatic vibrations will produce additional stimulation to the underlying tissue that the mechanical cymatic oscillations of the applicator-wand alone or the magnetic field alone cannot produce.

The application surface (3) is smooth and flexible.

The magnet (7) will be coupled securely to the transducer (6) as close to the application surface (3) as practical.

The device may be turned on or off by a switch (5) on the wand-like applicator (4).

The wand-like applicator may be flexibly connected to the Central Processing Unit (2) by means of an electric cable (1).

In order to enhance such magneto therapeutic properties, the applicator-wand may be moved in a variety of patterns over the affected body part.

The present invention in a second preferred embodiment further provides for the treatment of facial conditions by positioning a therapeutic mask-like apparatus (10) of the invention directly in contact with the skin or directly above the skin of the face. In a preferred embodiment, with reference to FIGS. 5, 6 and 7, an application surface (3) is mounted on a mask-like apparatus (10) which has apertures (11) over the eye, nose (12) and mouth (13) regions of the mask-like apparatus to allow maximum contact between the application surface (3) and the contours of the face while permitting the person being treated to breath easily. Different shapes and sizes of the mask-like apparatus (10) are possible and may include masks with no eye apertures to facilitate treatment of the entire eye area. The mask-like apparatus (10) is constructed of non-magnetic material and may be constructed of flexibly connected sections to optimize fit to faces of different contours, shapes and sizes. In one embodiment a magnetic field is generated by at least one powerful permanent magnet (7) situated close to the surface of the application surface (3) of the mask-like apparatus (10).

Figure 7:
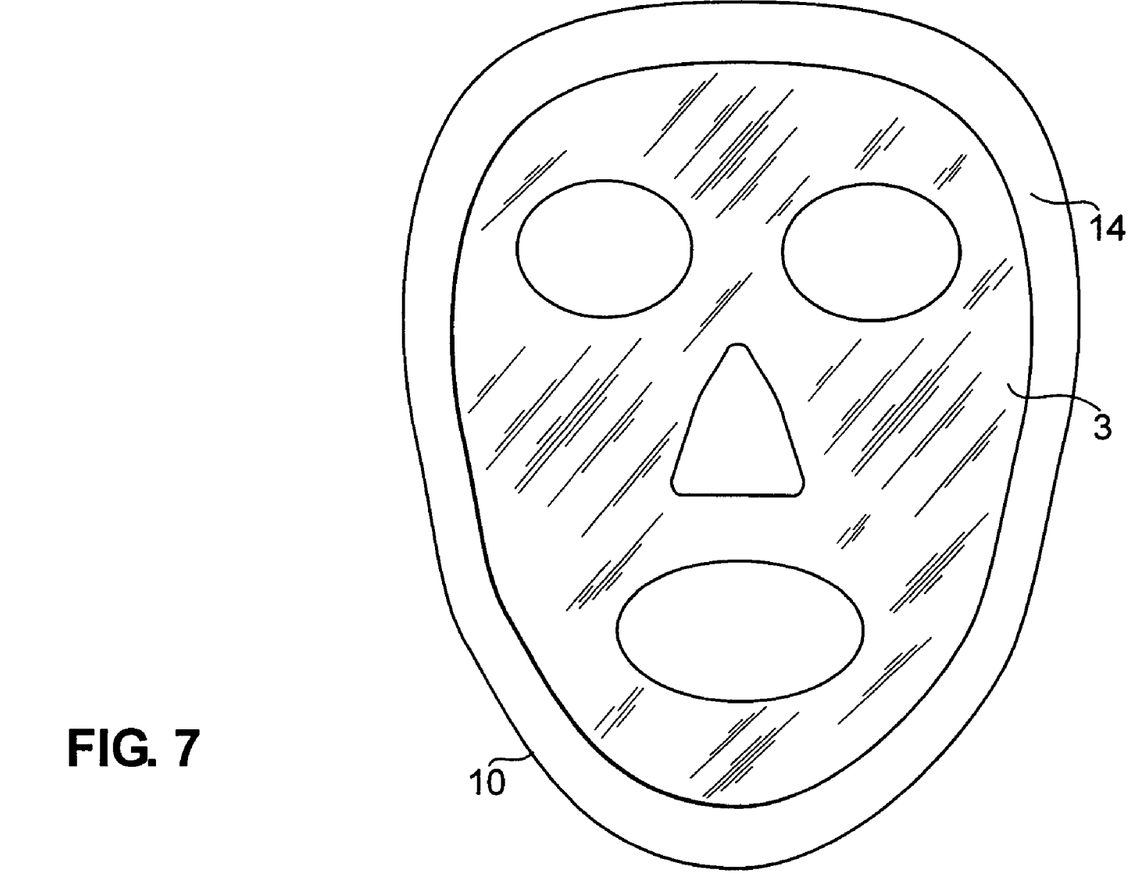

Removable foam rubber cushioning (14) around the outer edge of the interior side of the mask (10) permits the mask-like apparatus to be positioned above the face without directly contacting the skin of the face.

The application surface (3) on the interior side of the mask is smooth and flexible.

Figure 5:
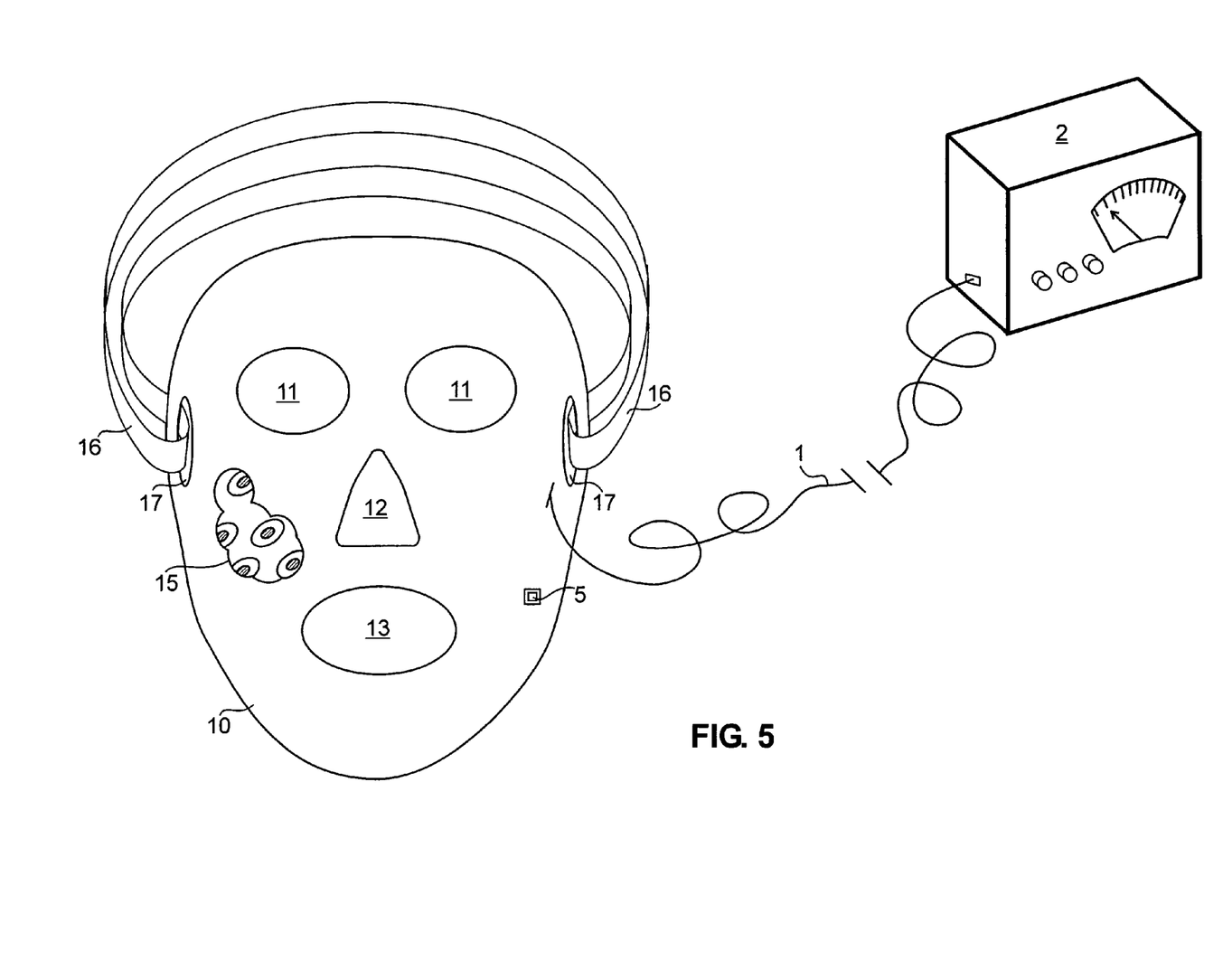
FIG. 5 is a second embodiment of the present invention in the form of a face mask.
Figure 6:
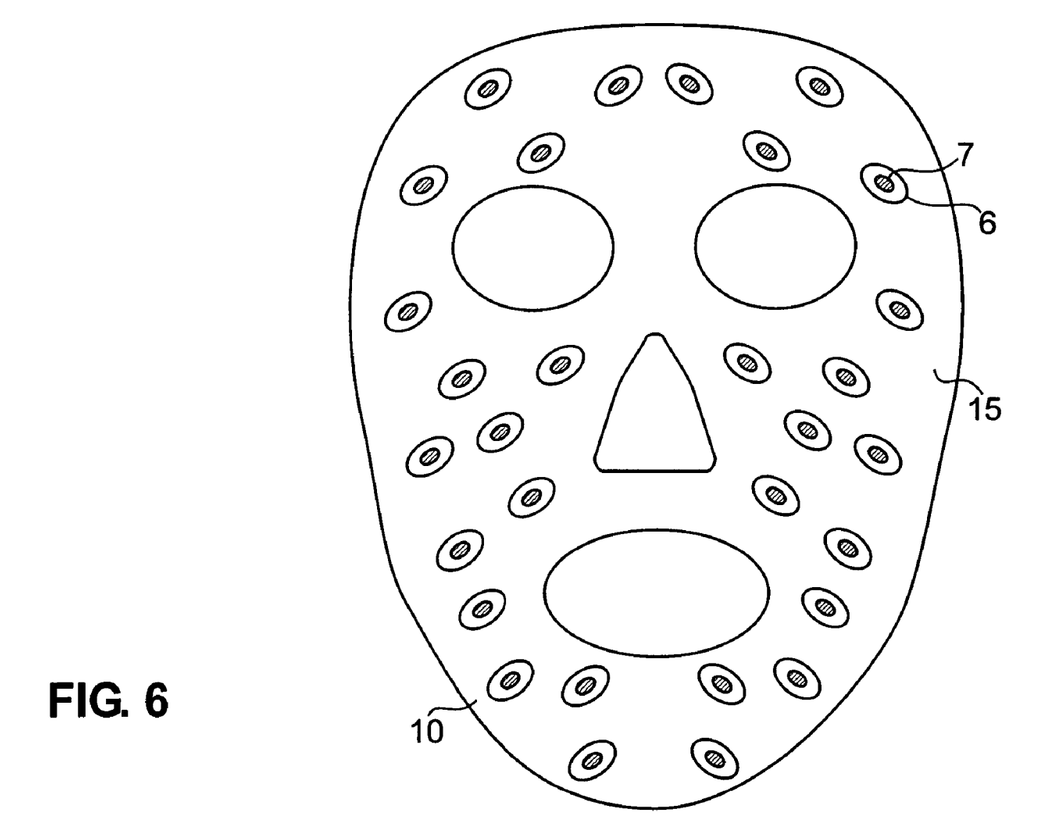
FIG. 6 shows how the multiple magnets and transducers maybe arranged in an array within the face mask; and, FIG. 7 is a view of the interior side of the face mask.

The magnet (7) will be coupled securely to the transducer (6) as close to the application surface (3) as practical.

The device may be turned on or off by a switch (5) on the mask-like apparatus (10) or on the Central Processing Unit (2).

The mask-like apparatus may be flexibly connected to the Central Processing Unit (2) by means of an electric cable (1).

In order to enhance such magneto-cymatic therapeutic properties, a plurality of magnets (7) each coupled to an individual transducer (6) may be arranged in an array (15) within the mask-like apparatus (10) as shown in FIGS. 5 and 6.

The face mask (10) may be optionally secured to the face by use of elastic straps (16) which loop through openings (17) in the mask (10).

By providing a twofold therapeutic approach whereby both magnetic and cymatic therapy are simultaneously provided, the present invention provides a mechanism by which better tissue therapy may be provided by the application of both methods or treatment regimes. There may be some synergistic effects provided in the simultaneous application of both magnetic therapy and cymatic therapy.

I claim:

1. Apparatus for providing concurrent magnetic therapy and cymatic therapy to the face, comprising:
    a first array of magnets, each of said magnets providing a magnetic field;
    a second array of transducers, wherein each of said transducers has a signal input and an operating state in which the transducer vibrates at a selected frequency responsive to said signal input;
    a central processing unit having an electrical signal output, said electrical signal output being selectable from among a range of audio frequencies;
    second array of transducers signal inputs being coupled to said central processing unit electrical signal output and said second array of transducers being mechanically coupled to said first array of magnets wherein said second array of transducers convert said central processing unit electrical signal at said audio frequency to mechanical vibrations at said frequencies; and
    whereby, simultaneous application of magnetic therapy and cymatic therapy occurs when said first array of magnets is placed in proximity to tissue to be treated and vibrated by said transducer.

2. The apparatus of claim 1, further comprising a housing wherein said first array of magnets and said first array of transducers are housed within said housing.

3. The apparatus of claim 2, wherein said housing comprises a non-magnetic material.

4. The apparatus of claim 3 wherein the housing further comprises a mask in which said non-magnetic material is disposed to be proximate said tissue to be treated.

5. The apparatus of claim 1 wherein said first array of magnets and said first array of transducers comprises a ratio of one transducer associated with one magnet.

6. A mask device for providing concurrent magnetic therapy and cymatic therapy, to treat wrinkles and tone facial muscles comprising:
    an exterior plastic casing, said plastic casing having at least one aperture associated with one of an eye, nose and mouth;
    an interior application surface;
    a central processing unit having an output providing electrical signals at selectable sound frequencies;
    an array of strongly magnetic magnets coupled to associated transducers;
    said transducers being responsive to said electrical signals and producing mechanical vibrations at said frequencies, said transducers being housed within said plastic casing and electrically connected to the central processing unit output;
    said magnets being permanently positioned between said transducers and said interior application surface;
    whereby, said mechanical vibrations generated by the transducers cause the magnets and the interior application surface to vibrate at said frequencies.

7. The device of claim 6, wherein said application surface is flexible.

8. The device of claim 7, wherein the magnets are selected from among the group consisting of neodymium, Samarian cobalt, ferrite, alnico and combinations thereof.

9. The device of claim 8, which further comprises elastic straps to secure the mask to the face being treated.

10. The device of claim 9 which further comprises a perimeter of foam rubber attached to the interior application surface.

11. A method of administering magneto-cymatic therapy to a person's face to treat wrinkles and facial muscle tone comprising; positioning an array of magnets in proximity to the face to be treated and vibrating said positioned array of magnets at a first frequency for an effective amount of time; and vibrating said positioned array of magnets at a first frequency mechanically vibrated at said first frequency to provide simultaneous application of magneto therapy and cymatic therapy.

12. The method of claim 11 wherein vibrating said array of magnets further comprises providing a central processing unit and a plurality of transducers, the central processing unit having a plurality of electric signal outputs corresponding to a plurality of cymatic frequencies, coupling said central processing unit to transducers capable of converting said electric signals to mechanical vibrations at said cymatic frequencies, coupling said transducers to said array of magnets, and selecting said electrical signal outputs and thereby vibrating said array of magnets at the frequencies corresponding to said selected electric signals.

* * * * *

UNITED STATES PATENT AND TRADEMARK OFFICE
CERTIFICATE OF CORRECTION

PATENT NO. : 6,971,984 B2  
APPLICATION NO. : 10/893120  
DATED : December 6, 2005  
INVENTOR(S) : Vincent Ardizzone

Page 1 of 1

It is certified that error appears in the above-identified patent and that said Letters Patent is hereby corrected as shown below:

Please replace "Item (73) Assignee: Vincent Ardizzone, Port Jefferson, NY (US)" with --Item (73) Assignee: Cymatics International, Inc., Port Jefferson, NY (US)--.

Signed and Sealed this

Twelfth Day of December, 2006

JON W. DUDAS
*Director of the United States Patent and Trademark Office*